(12) United States Patent  
Schulz et al.

(10) Patent No.: US 6,540,668 B1
(45) Date of Patent: Apr. 1, 2003

(54) ENDOSCOPE WITH A COUPLING DEVICE (VIDEO COUPLER) FOR CONNECTION OF A VIDEO CAMERA

(75) Inventors: Dieter Schulz, Muehlheim (DE); Norbert Haeckl, Leibertingen (DE); Rainer Brunnen, Seitingen (DE); Thomas E. Roehm, III, Braden, TN (US)

(73) Assignees: Henke-Sass, Wolf GmbH, Tuttlingen (DE); Sofamor Danek Group Inc., Surgical Navigation Technologies, Memphis, TN (US)

( * ) Notice: Subject to any disclaimer, the term of this patent is extended or adjusted under 35 U.S.C. 154(b) by 0 days.

(21) Appl. No.: 09/464,180

(22) Filed: Dec. 16, 1999

(30) Foreign Application Priority Data

Dec. 21, 1998 (DE) .......................................... 198 59 155

(51) Int. Cl.⁷ ............................................. A61B 1/04
(52) U.S. Cl. ...................................... 600/112; 600/167
(58) Field of Search ...................... 600/112, 167–168, 600/162–164, 114, 138; 359/822, 823, 825, 826, 819, 694, 382–383, 425

(56) References Cited

U.S. PATENT DOCUMENTS

| | | | |
|---|---|---|---|
| 3,161,716 A | * 12/1964 | Burris | .......................... 359/427 |
| 4,611,888 A | 9/1986 | Prenovitz et al. | |
| 4,844,071 A | * 7/1989 | Chen | ........................... 600/112 |
| 4,969,450 A | 11/1990 | Chinnock et al. | |
| 5,418,645 A | * 5/1995 | Coath et al. | .................. 359/676 |
| 5,528,432 A | * 6/1996 | Donahoo | ..................... 359/894 |
| 5,575,754 A | * 11/1996 | Konomura | ................... 600/117 |
| 5,762,605 A | * 6/1998 | Cane | ........................... 600/200 |
| 5,808,813 A | * 9/1998 | Lucey | ......................... 359/694 |
| 6,019,721 A | * 2/2000 | Holmes | ...................... 600/167 |
| 6,059,721 A | * 5/2000 | Rudischhauser | ............ 600/167 |
| 6,113,533 A | * 9/2000 | Howes | ........................ 600/112 |
| 6,346,076 B1 | * 2/2002 | Rovegno | .................... 600/173 |
| 6,203,492 B1 | * 3/2002 | Davis | ......................... 600/101 |

FOREIGN PATENT DOCUMENTS

DE      195 13 930 A1      9/1996

OTHER PUBLICATIONS

English Abstract of DE 195 13 930 A1.

* cited by examiner

*Primary Examiner*—Denise M. Pothier
(74) *Attorney, Agent, or Firm*—Reed Smith LLP

(57) ABSTRACT

An endoscope with a coupling device for the connection of a video camera, wherein the endoscope has, at its needle-shaped tube, a distal end which is provided for insertion into the body and a lens system and has a proximal end provided for looking into the endoscope and having a field diaphragm, the coupling device being attached to the proximal end, and wherein a lens system is arranged following the field diaphragm and, like the lens system at the distal end, is sealed off from the outside completely and tightly and is constructed so as to be non-adjustable and non-focusable. The coupling device has no lenses and is adjustable with respect to its axial length in the manner of a telescope.

10 Claims, 7 Drawing Sheets

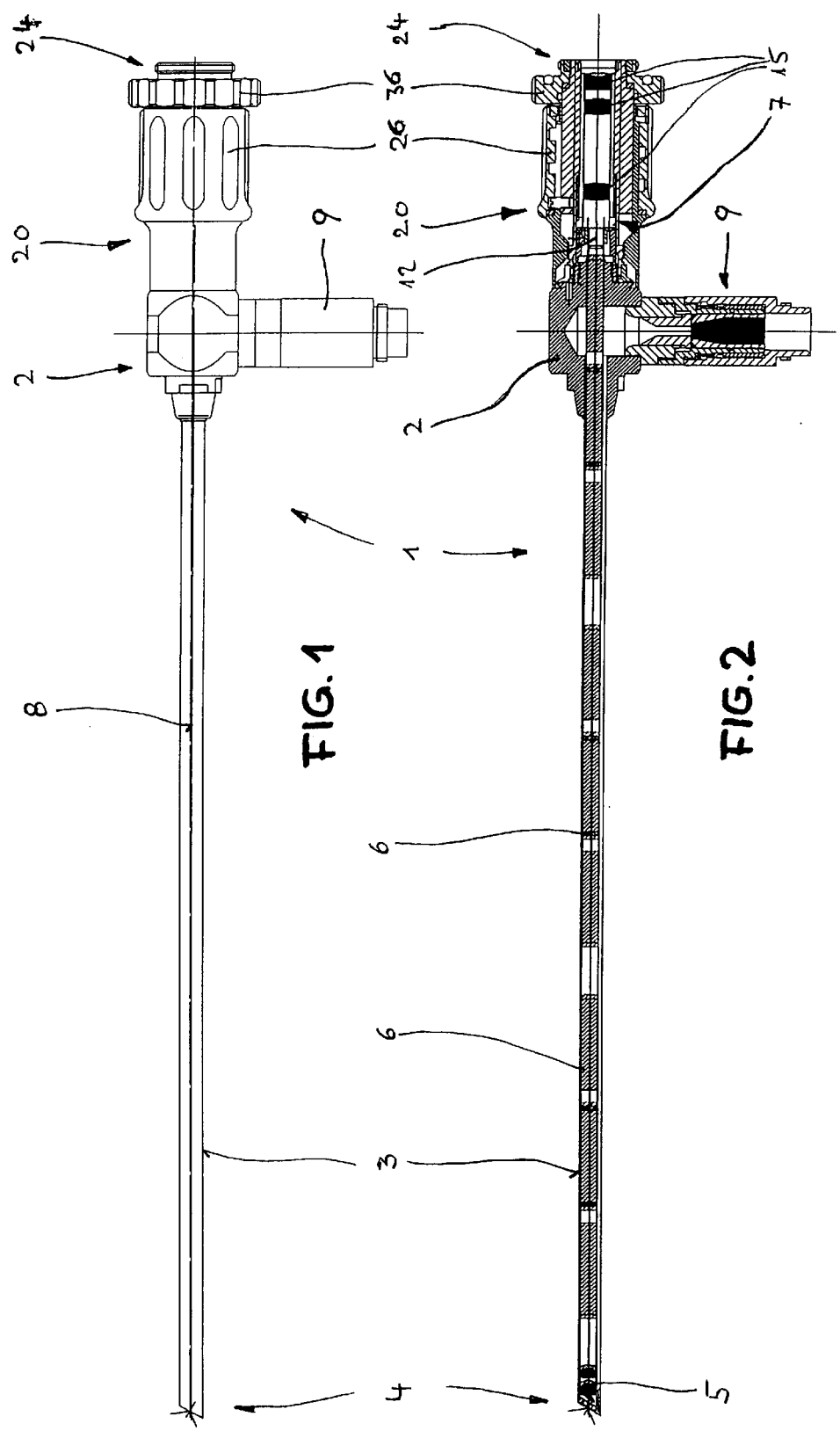

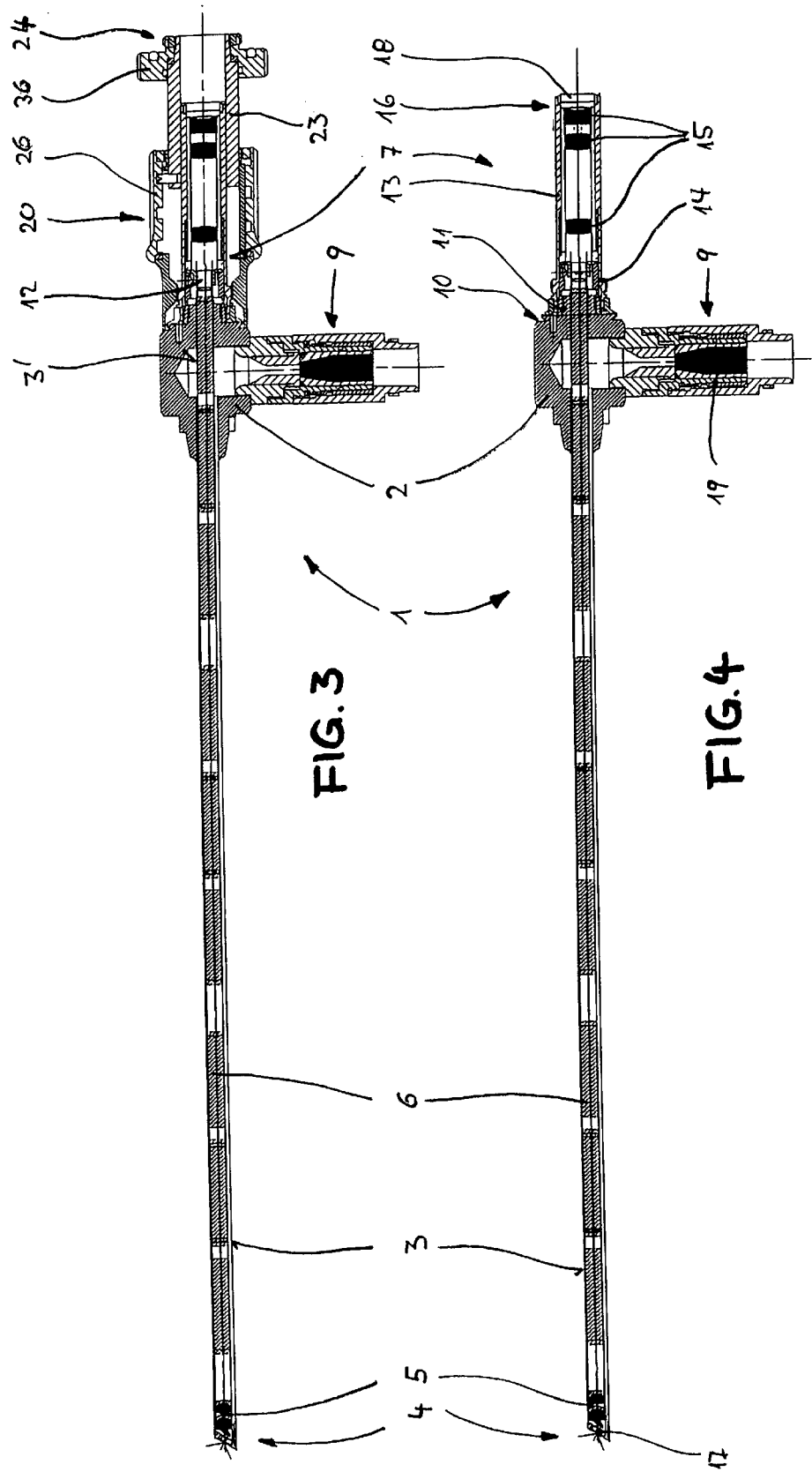

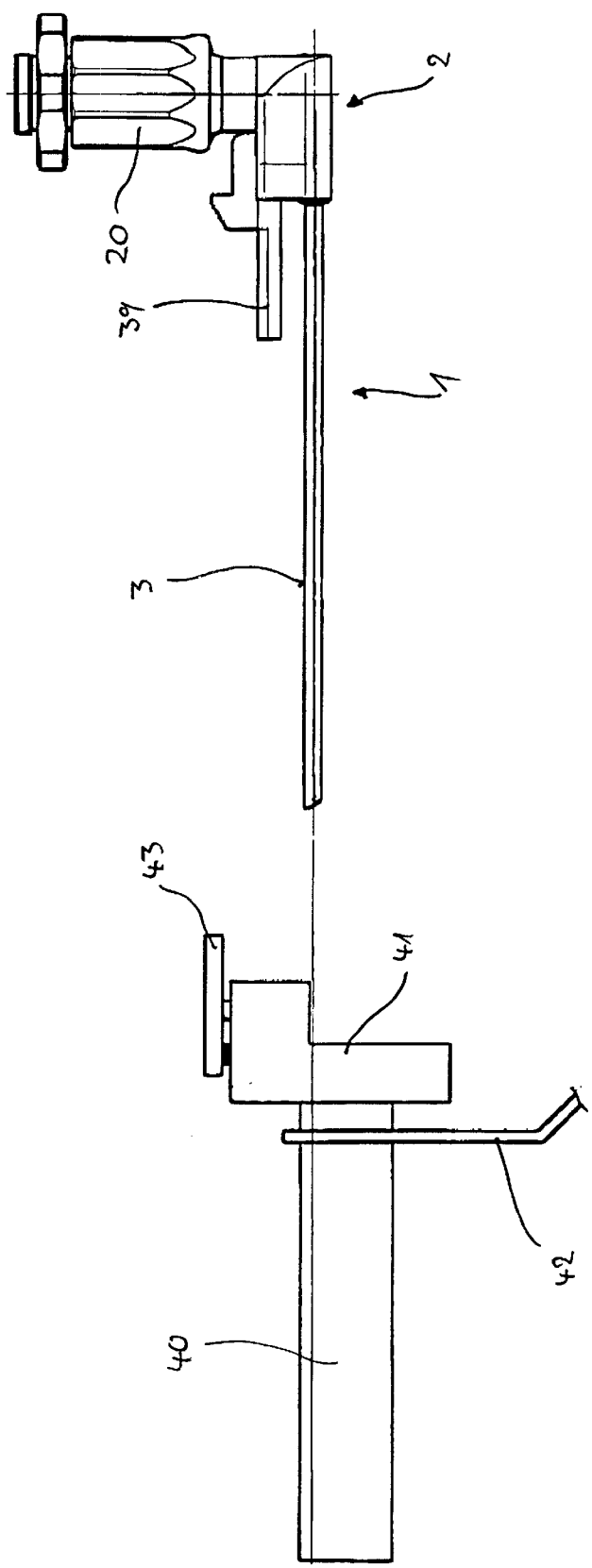

ENDOSCOPE WITH A COUPLING DEVICE (VIDEO COUPLER) FOR CONNECTION OF A VIDEO CAMERA

BACKGROUND OF THE INVENTION a) Field of the Invention

The invention is directed to an endoscoping arrangement comprising an endoscope with a needle-shaped tube which has a lens system on its distal end provided for insertion into the body, and with a viewing field diaphragm provided at a proximal viewing-side end of the endoscope, and a coupling device for connection of the endoscope to a video camera, the coupling device being attachable to the proximal end of the endoscope.

b) Description of the Related Art

A known endoscope of the type mentioned above is described as a videoarthroscope in U.S. Pat. No. 4,969,450. In this known endoscope, the proximal end of the needle-shaped tube on the one hand and the distal end of the coupling device on the other hand are attached to a middle part which has a connection for a light source, the light coming from the light source being guided by a glass fiber bundle contained in the connection via the middle part through the tube-shaped needle to the distal end of the latter.

The coupling device has a first lens system facing a field diaphragm provided on the proximal end of the needle-shaped tube and another, second lens system on its proximal end, facing the video camera, wherein the first lens system is fastened in a sleeve which is mounted in a coupling device so as to be longitudinally displaceable, so that the image transmitted by the endoscope and the lens transmission and image transmission system contained in the needle-shaped tube, respectively, can be focused and correspondingly transmitted to the CCD chip contained in the video camera. For this purpose, the coupling device has on its outside a sleeve-shaped actuating member that can be rotated around its longitudinal axis and with which the first lens system can be moved in an axial direction.

Endoscopes outfitted with video cameras and having an eyepiece fixedly attached to their proximal end are also known. In endoscopes of this type, the coupling device which can be focused and which is necessary for the connection of the video camera is attached at or to the eyepiece, for example, by means of suitably constructed clamping devices. Apart from the fact that such endoscopes and coupling devices can principally not be autoclaved, the form of fastening the coupling device to the eyepiece also represents a very unstable fastening device.

It is absolutely indispensable for endoscopes to be sterilized perfectly, i.e., so as to be completely free of germs, after use or before being put to use again. However, freedom from germs is only guaranteed if the instrument can be autoclaved, that is, exposed to very high temperatures and pressures. In the case of the known endoscope with its coupling device for connection of the video camera, autoclaving is not possible because, in view of the above-described adjustability of the lens system contained in the coupling device, it cannot be constructed in a sufficiently tight and hermetically sealed manner to prevent hot steam from entering into the coupling device and accordingly rendering opaque the lenses contained therein. For this reason, these endoscopes and coupling devices are merely put into sterilizing solutions and are consequently not as well sterilized as they would be when autoclaved.

OBJECT AND SUMMARY OF THE INVENTION

Therefore, it is the primary object of the invention to provide an endoscope with a coupling device for connection of a video camera, both of which can be autoclaved completely, possibly together, as the case may be, that is, without the need for disassembly.

This object is met for an endoscope arrangement of the type mentioned in the introduction in that the endoscope has, at its proximal end, a lens system which follows the field diaphragm and which, like the lens system at the distal end, is completely and tightly sealed off from the outside and is not adjustable/cannot be focused, and in that the coupling device does not have a lens and is adjustable along its axial length in the manner of a telescope.

Due to the fact that a lens system which cannot be adjusted/focused is provided at the proximal end of the endoscope following the field diaphragm, the endoscope, including its middle part and its light connection and the two ends of the tube, can be hermetically sealed toward the outside and can therefore be autoclavable in its entirety. Furthermore, since a lens system is arranged in the proximal end of the endoscope, it is no longer necessary to arrange a lens system in the coupling device; it is sufficient for the latter to be designed in such a way that it can change the distance between the CCD chip arranged in the video camera, which records the image of the operating field supplied by the endoscope, and the lens system arranged in the proximal end of the endoscope. Accordingly, the coupling device can be constructed as a simple telescope-like, hollow-cylindrical body which can be fully autoclaved like the hermetically sealed endoscope.

In a further advantageous development of the invention, the coupling device has a sleeve-shaped shaft of a certain length whose distal end is designed to be fastened to the endoscope, and a focusing sleeve is inserted in the shaft so as to be longitudinally displaceable, a fastening device for connection of the video camera or an eyepiece being provided at the proximal end of the focusing sleeve.

This construction of the coupling device ensures that the video camera which is connected to the proximal end of the focusing sleeve by means of the fastening device can be adjusted, along with its CCD chip, with respect to distance relative to the proximal end of the endoscope, that is, can be adjusted so as to be more or less far away. In this way, the image of the operating field delivered by the endoscope is focused mechanically on the CCD chip of the video camera or on the retina of the eye of the observer looking into the eyepiece which is mounted in place of the video camera at the proximal end of the focusing sleeve.

According to the invention, the shaft is surrounded by an adjusting sleeve, there being formed in the inside wall of the adjusting sleeve a groove which is shaped like or which follows a course like a thread and has a relatively large pitch, and the focusing sleeve has a radial pin projecting outward on its distal end, for example, in the shape of a pin-shaped screw, which projects into the groove of the adjusting sleeve through an axially extending slit provided in the shaft.

This special construction of the coupling device ensures that the focusing sleeve does not twist inside the shaft and only moves in an axial direction when the adjusting sleeve is actuated.

The adjusting sleeve is advantageously mounted on the shaft so as to be rotatable and so as to prevent an axial displacement thereon between two stops which are formed at the shaft and arranged at a distance from one another.

This special construction of the adjusting sleeve ensures that the focusing sleeve can be displaced inside the shaft simply by rotating it.

In a further advantageous development the pin is constructed as a pin-shaped screw that is screwed into a bore hole provided in the focusing sleeve. This construction of the pin effecting the longitudinal displacement of the focusing sleeve permits a relatively simple construction of the focusing sleeve in which only a radial bore hole must be provided; the pin-shaped screw can then be screwed into this radial bore hole.

The screw has a circumferentially extending projection which projects radially outward and which is formed on the outer wall of the focusing sleeve as a stop for limiting the screw-in depth.

Accordingly, the screw-in depth or the distance by which the pin-shaped screw projects radially beyond the outer radius of the focusing sleeve are determined in a simple manner.

Finally, the fastening device for connection of the video camera or an eyepiece is advantageously realized as an adjusting ring rotatably mounted on the proximal end of the focusing sleeve.

The fastening device can be turned by means of this adjusting ring and the video camera or the eyepiece can thus be turned in its position relative to the endoscope, depending on how the image of the operating field received by the endoscope is to be represented.

Also, an eyepiece can be provided on the proximal end of the coupling device instead of the video camera, so that the user of the endoscope has the option of looking into the endoscope himself, that is, without using a video camera or a video setup.

In an advantageous further development of the endoscoping arrangement, the beam path of the endoscope between the lens system in the distal end and the lens system in the proximal end is deflected by means of an intermediately arranged prism, and the deflection is provided adjacent to the field diaphragm.

The arrangement of a deflection of this kind by means of a prism in the above-described area, that is, in front of the lens system in the proximal end of the endoscope and, in particular, in front of the coupling device without any lenses, makes possible an endoscope design in which the connection part for the video camera is outside of the immediate radial working area of the tube of the endoscope.

It is advantageous for the prism to be a 90-degree or right-angle prism; this results in a maximal deflection of the connection part for the video camera out of the working area of the endoscope.

In a further advantageous development, the endoscope has, in the area of deflection, a connection piece for mounting an operating shaft which is not described more fully in this application. Through the operating shaft, the operator can operate in connection with the endoscope, in particular the tube of the endoscope, and at the same time observe the operating field more accurately without being obstructed by the connected video camera.

The operating shaft advantageously has a receiving piece adapted to the connection piece of the endoscope. With this receiving piece, the operating shaft can be connected to the endoscope in a simple manner and in a precisely fixed position.

In a further advantageous development, the receiving piece contains a locking mechanism that enters into a positive engagement with the connection piece when the receiving piece is slid onto the connection piece. This special construction of the receiving piece in connection with the connection piece results in a stable and secure connection between the endoscope and the operating shaft.

Embodiment examples of the endoscope with a coupling device for connection of a video camera that do not limit the invention are described in the following with reference to the figures represented in the drawings.

BRIEF DESCRIPTION OF THE DRAWINGS

In the drawings

FIG. 1 shows a side view of an endoscope with attached coupling device, but without a video camera;

FIG. 2 shows a section through the endoscope according to FIG. 1;

FIG. 3 shows a section through the endoscope according to FIG. 2 but with the coupling device fully extended;

FIG. 4 shows a section through the endoscope without the attached coupling device;

FIG. 11 shows a view of an operating shaft with a prism-shaped receiving piece;

FIG. 12 shows a view of the endoscope in the embodiment form according to FIGS. 9 and 10.

DESCRIPTION OF THE PREFERRED EMBODIMENTS

Figure 5:
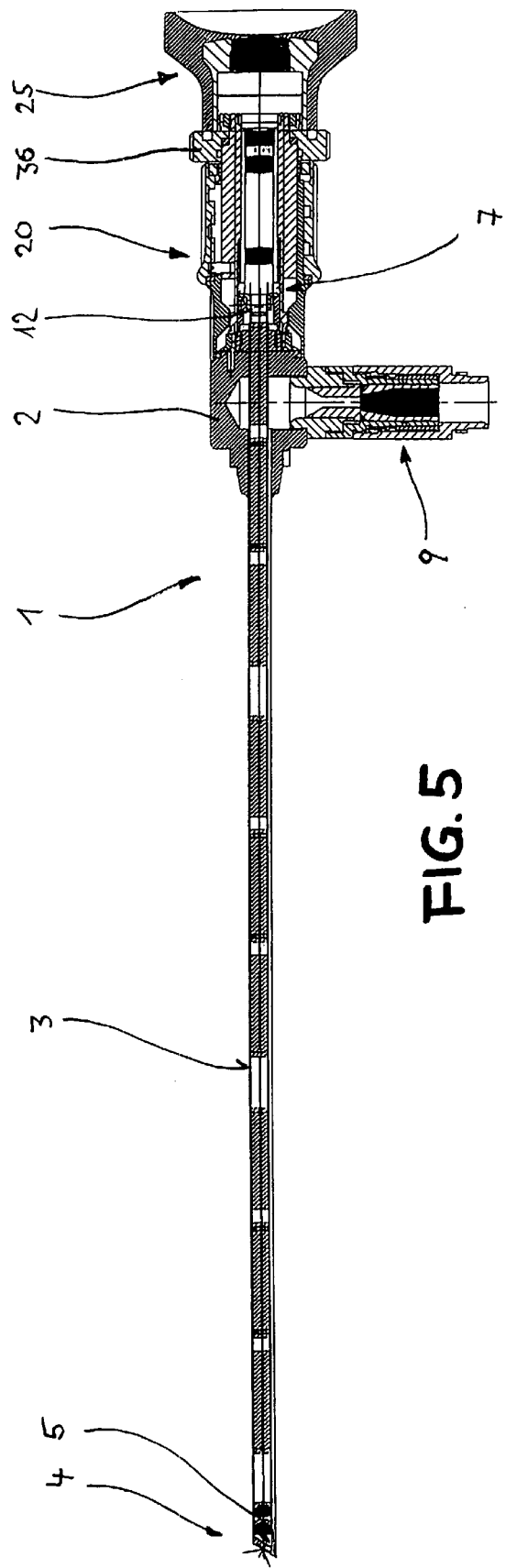
FIG. 5 shows a section through the endoscope according to FIG. 2, but with the eyepiece attached.

The endoscope 1 shown in the Figures has a middle part 2 to which is fastened a needle-shaped tube 3 intended for insertion into an operating field and having, in its distal end 4, a lens system 5 for receiving the operating field. Arranged inside the tube 3 there is a further, second tube 3' of a smaller diameter in which are arranged rod lenses 6 at distances to one another and possibly other lenses or lens systems which convey the image of the operating field received by the lens system 5 at the distal end 4 to the proximal end 7 of the endoscope, this proximal end 7 being held by the middle part 2. Also arranged at the middle part 2 is a connecting sleeve 9 which is arranged at right angles to the longitudinal axis 8 of the tube 3 or endoscope 1 and provided for the arrangement of a light-conducting cable, not shown, through which the light delivered by a light source, also not shown, and transmitted by the light-conducting cable can be conducted, e.g., via glass fibers, through the middle part 2 and through the tube 3 to the distal end 4 of the tube 3 and, accordingly, onto the operating field.

The second tube 3' is guided through the middle part 2, exits on the rear side 10 of the middle part 2 facing the video camera, not shown in the drawings, and ends at a connection piece 11 provided on this rear side 10. A field diaphragm 12 is provided in this end of the tube 3'.

A tubular shaft 13 is fastened, e.g., screwed, to the connection piece 11 by its distal end 14; this contains a lens arrangement 15 which is fixedly built into the shaft 13, i.e., it cannot be focused but, rather, delivers a finished picture of the operating field in connection with the lens systems 5, 6 arranged in the tube 3'.

The tube 3 and the shaft 13, respectively, have hermetically sealed windows 17 and 18 at the distal end 4 as well as at the proximal end 16. A closure 19 of this kind, which seals hermetically but also transmits light, is also provided in the connecting sleeve 9, so that it is possible for the endoscope shown in FIG. 4 to be completely autoclavable, i.e., the endoscope 1 can, in this form, withstand the high temperatures and pressures occurring during autoclaving without damage to the lens systems and therefore without impairing the quality of the image transmission.

Figure 7:
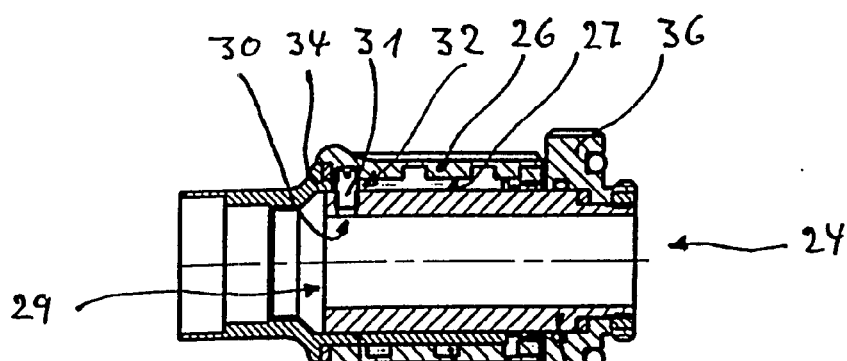
FIG. 7 shows a section through the coupling device in its moved in position.
Figure 8:
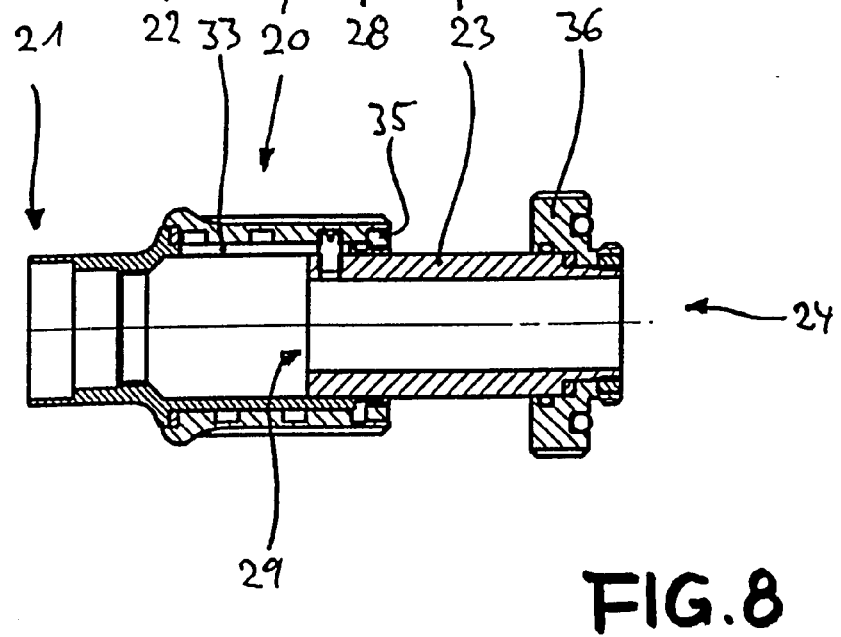
FIG. 8 shows a section through the coupling device in its fully extended position.

For transmitting the image of the operating field generated by the above-described endoscope to the CCD chip of the video camera, not shown in the drawings, or to the retina of the eye of an observer wishing to look directly through the endoscope, a coupling device 20 is provided, of which a section is shown in FIGS. 7 and 8; this coupling device 20 is pushed over the shaft 13 and fastened to the distal end 14 thereof and abuts against the rear side 10 of the middle part 2 so as to engage over the connection piece 11.

In contrast to known endoscopes with a coupling device for connection of a video camera, the coupling device 20 has no lenses, i.e., only mechanical focusing is possible, but not optical focusing. This is possible for the endoscope 1 according to the invention because, as was already described above, it has a fixedly installed lens combination 15 at its proximal end 7, namely, inside the shaft 13, which in connection with the other lens systems 5 and 6 of the endoscope 1 and field diaphragm 12 already delivers a finished image of the operating field.

There only remains now for this image of the operating field delivered by the hermetically closed and therefore autoclavable endoscope 1 to be projected onto the CCD chip of the video camera in such a way that it can be transmitted to the video system perfectly and with the highest-quality clarity. For this purpose, the coupling device 20 shown in section especially in FIGS. 7 and 8 enables a "mechanical focusing" in that the distance of the CCD chip of the video camera fitted to the proximal end 21 of the coupling device 20 from the window 18 in the proximal end 16 of the shaft 13 on which the coupling device 20 is arranged can be varied.

Figure 6:
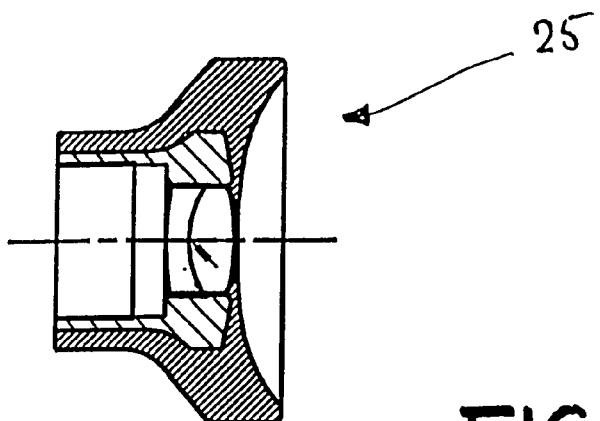
FIG. 6 shows a section through the eyepiece.

For this purpose, the distal end 21 of the coupling device 20 is essentially realized as a sleeve-shaped shaft 22 of a certain length into which a focusing sleeve 23 has been inserted in such a way that it can be displaced longitudinally, a fastening device for the connection of the video camera or of an eyepiece 25 being provided at the proximal end 24 of this focussing sleeve 23. By means of the eyepiece 25 illustrated in FIG. 6, the operating field can be viewed directly through the endoscope 1.

The shaft 22 is surrounded by an adjusting sleeve 26, in the inside wall 27 of which there is a groove 28 shaped like or following a course like a thread and having a relatively large pitch.

The focusing sleeve 23 has at its distal end 29 a radial bore hole 30 into which is screwed a pin-shaped screw 31 having a stop 32 in the shape of a circumferentially extending projection which limits the insertion depth or screw-in depth. The pin-shaped portion of the screw 31 projecting over the outer circumference of the focusing sleeve 23 extends through an axial slit 33 provided in the shaft 22 and into the groove 28 in the adjusting sleeve 26. This adjusting sleeve 26 is rotatably mounted on the shaft 22 between two stops 34 and 35 formed at the shaft 22 so as to prevent an axial displacement of the adjusting sleeve 26.

When the adjusting sleeve 26 is rotated, the helical groove 28 into which the screw 31 projects is rotated along with it. In this way, the latter, and accordingly also the focusing sleeve 23, is displaced in the longitudinal direction inside the axial slit 33 of the shaft 22, so that a change of the distance from the eyepiece 25 or video camera attached to the proximal end 24 to the window 18 of the endoscope 1 is effected and the image transmitted from the endoscope 1 is sharply imaged on the CCD chip or on the retina of the eye of the observer looking through the eyepiece 25.

The fastening device provided at the proximal end 24 of the focusing sleeve 23 for the video camera or the eyepiece 25 is constructed as an adjusting ring 36 which is rotatable on the proximal end 24, so that the eyepiece 25 or the video camera can be rotated by 360° on the focusing sleeve 23.

Figures 9, 10:
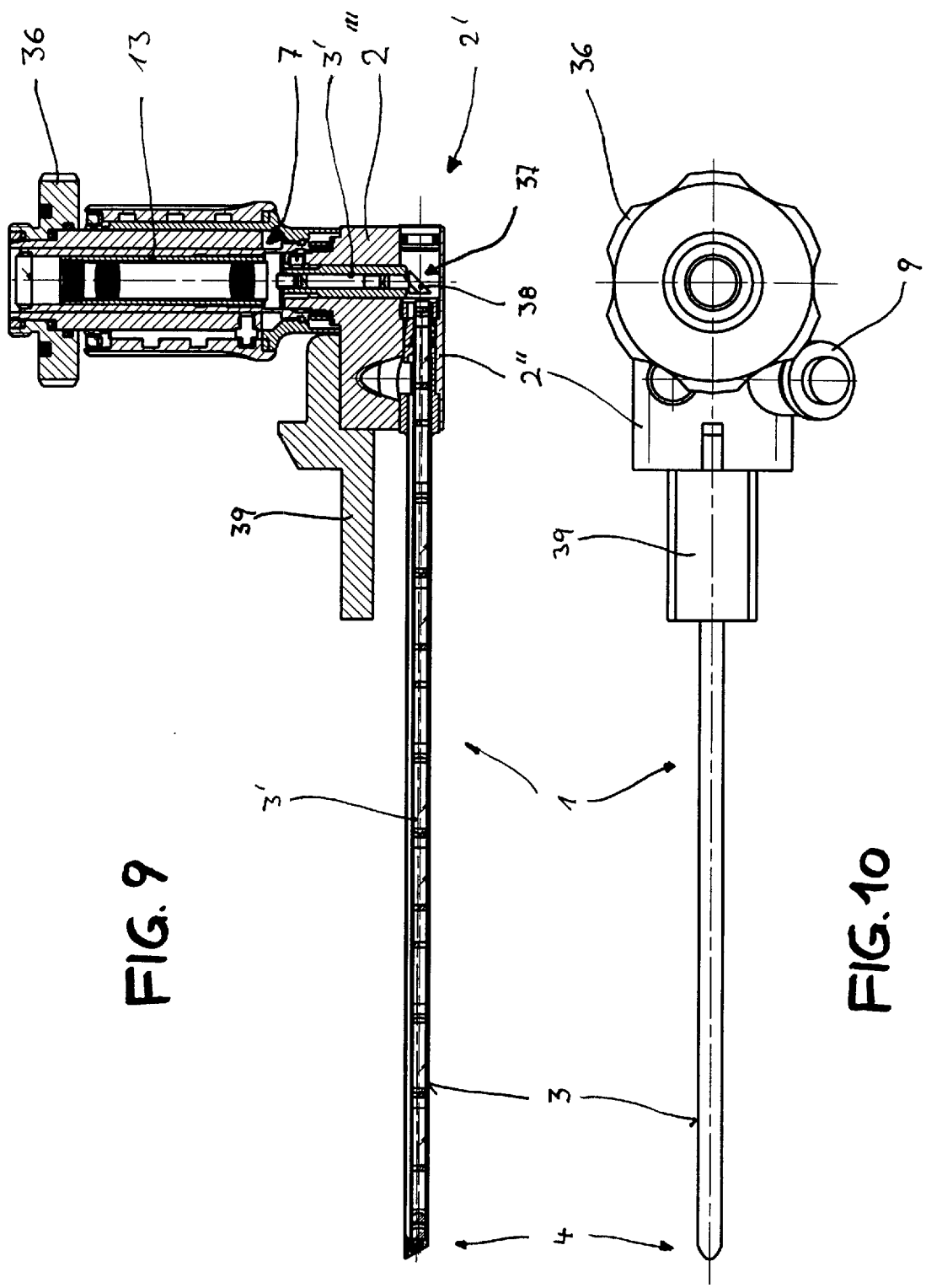
FIG. 9 shows a section through the endoscope in the embodiment form with a beam path deflected by 90° in the area of the middle part.
FIG. 10 shows a view of the endoscope according to FIG. 9, in particular of the coupling device bent at an angle.

A special embodiment form of the endoscope according to the invention is shown in FIGS. 9 and 10. In this embodiment form, the linear beam path from the distal end 4 of the endoscope 1 through the inner tube 3' to the proximal end 7 of the endoscope 1 is interrupted in the area 37 of the specially designed middle part 2' where a right-angle prism 38 is arranged, so that the optical beam path is changed in direction by 90°. For this purpose, the middle part 2' is approximately bent at an angle, wherein the side 2" of the middle part 2' facing the distal end 4 of the endoscope 1 holds the needle-shaped tube 3, and the side 2'" of the middle part 2' facing the proximal end 7 of the endoscope 1 guides the proximal portion of the inner tube 3' at an angle of 90° to the proximal end 7 or to the tubular shaft 13 having the lens system 15. By means of this deflection of the optical beam path by 90°, it is possible to attach the coupling device 20, or the video camera to be connected thereto, laterally at the endoscope arrangement and to keep the area radially around the tube 3 of the endoscope free, so that it can be used as a working area especially for the attachment of an operating shaft 40. This operating shaft 40 which is, for example, shaped like a tube and has a diameter which is appreciably greater that the diameter of the tube 3 of the endoscope 1 can be fastened to a connection piece 39 formed at the middle part 2', in particular at the part 2" of the middle part 2', and, because of the lateral arrangement of the coupling device 20, the operator can operate through the operating shaft 40 with the instruments located therein without being impeded.

Due to the fact that the coupling device 20 is constructed, according to the invention, without lenses and can be mounted and operated in a simple manner on the tightly sealed and therefore autoclavable proximal end 7 of the endoscope 1, it is possible for the endoscope 1 itself to have not only a straight-line configuration with respect to its optical beam path, but also an angled configuration, for example, a 90-degree deflection, as has been described above and shown in the embodiment example in FIGS. 9 and 10. Without in any way disadvantageously affecting the lens system 15 located in the proximal end 7 of the endoscope 1, the beam path can be deflected in the inner tube 3' in the area of the middle part 2 or 2' by a prism to be provided in that area; the middle part 2' can additionally be constructed in such a way that it comprises not only the connecting sleeve 9 for the attachment of a light-conducting cable, but also a connection piece 39 for the attachment of an operating shaft 40.

Figure 13:
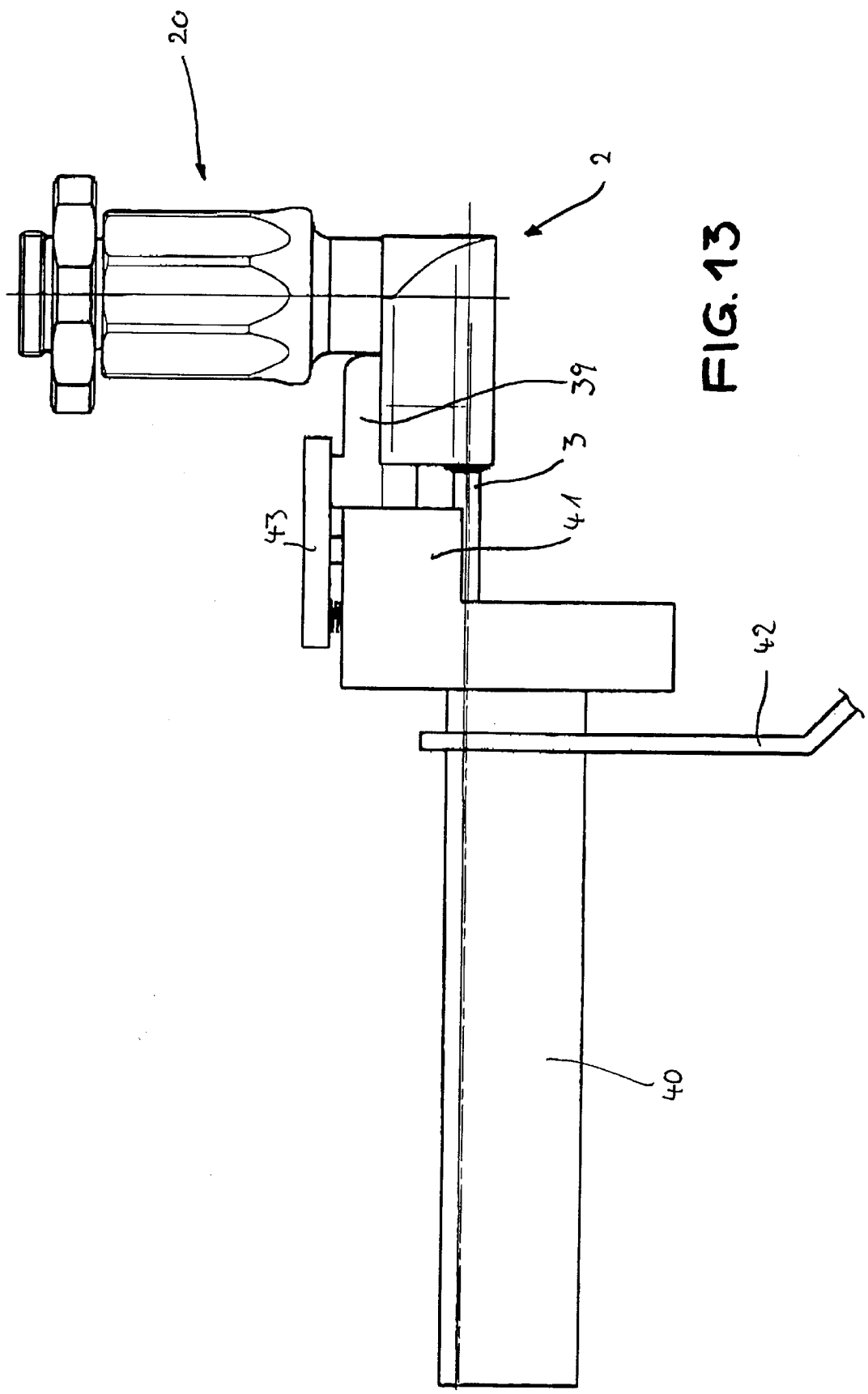
FIG. 13 shows a view of the endoscope in assembly with the operating shaft.

The operating shaft 40 is shown in FIG. 11 and has, at its proximal end, a prism-shaped receiving piece 41 which can be connected to the connection piece 39 of the endoscope 1 as is shown in FIG. 12. The operating shaft 40 and the endoscope 1 are shown in the assembled state in FIG. 13. FIG. 13 in particular shows how the coupling device 20 that is deflected by 90° leaves a relatively large free space for the operation of operating instruments for the operator when the endoscope 1 is used together with the operating shaft 40 in the area of the connection area between the connection piece 39 and the receiving piece 41 of these devices. The holder 42 attached to the operating shaft 40 serves as fastening means for holding devices which are to be specially provided and which are not described in more detail or shown in the Figures.

The receiving piece 41 has a locking mechanism 43 which enters into a positive engagement with the connection piece 39 on the endoscope 1 when the receiving piece 41 with the operating shaft 40 is pushed over the tube 3 of the endoscope and onto the connection piece 39.

While the foregoing description and drawings represent the present invention, it will be obvious to those skilled in the art that various changes may be made therein without departing from the true spirit and scope of the present invention.

What is claimed is:

1. An endoscope arrangement comprising:
    an endoscope with a needle-shaped tube which has a hermetically sealed lens system at a distal end intended for insertion into a body;
    a field diaphragm provided at a proximal viewing end of the endoscope;
    a coupling device for connecting the endoscope to a video camera;
    said coupling device being attachable to a proximal viewing end of the endoscope;
    said endoscope having, at its proximal viewing end, a second hermetically sealed lens system which is arranged following said field diaphragm;
    said first hermetically sealed lens system at a distal end and said second hermetically are constructed so as to be non-adjustable and non-focusable;
    wherein said coupling device has no lenses and is adjustable with respect to its axial length in the manner of a telescope;
    wherein the coupling device has a sleeve-shaped shaft of a certain length whose distal end is designed to be fastened to the endoscope, and wherein a focusing sleeve is inserted in the shaft so as to be longitudinally displaceable, a fastening device for connection of the video camera or an eyepiece being provided at the proximal end of the focusing sleeve;
    said shaft being surrounded by an adjusting sleeve, there being formed in the inside wall of the adjusting sleeve a groove which is shaped like a thread and which has a relatively large pitch, and wherein the focusing sleeve has a pin which projects out radially at its distal end, in the shape of a pin-shaped screw, which projects into the groove of the adjusting sleeve through an axially extending slit provided in the shaft.

2. The endoscope arrangement according to claim 1, wherein the adjusting sleeve is mounted on the shaft so as to be rotatable and so as to prevent an axial displacement thereon between two stops and which are formed at the shaft and arranged at a distance from on another.

3. The endoscope arrangement according to claim 1, wherein the pin is constructed as a pin-shaped screw that is screwed into a bore hole provided in the focusing sleeve.

4. The endoscope arrangement according to claim 3, wherein the screw has a circumferentially extending projection which projects radially outward and which is formed on the outer wall of the focusing sleeve as a stop for limiting the screw-in depth.

5. The endoscope arrangement according to claim 1, wherein the fastening device for connection of the video camera or an eyepiece is an adjustable ring which is rotatably mounted on a proximal end of the focusing sleeve.

6. The endoscope arrangement according to claim 1, wherein the beam path of the endoscope between the lens system in the distal end and the lens system in the proximal end is deflected by means of an intermediately arranged prism, and the deflection is provided adjacent to the field diaphragm.

7. The endoscope arrangement according to claim 6, wherein the prism is a right-angle prism.

8. The endoscope arrangement according to claim 6, wherein the endoscope has, in the area of deflection, a connection piece with an operating shaft mounted thereon.

9. The endoscope arrangement according to claim 8, wherein the operating shaft has a receiving piece adapted to the connection piece of the endoscope.

10. The endoscope arrangement according to claim 9, wherein the receiving piece has a locking mechanism that enters into a positive engagement with the connection piece when the receiving piece is slid onto the connection piece.

* * * * *